(12) United States Patent
Roerink et al.

(10) Patent No.: US 8,008,001 B2
(45) Date of Patent: Aug. 30, 2011

(54) PCV-2 VACCINE

(75) Inventors: Frank Roerink, Boxmeer (NL); Peter Van Woensel, Boxmeer (NL)

(73) Assignee: Intervet International B.V., Boxmeer (NL)

( * ) Notice: Subject to any disclaimer, the term of this patent is extended or adjusted under 35 U.S.C. 154(b) by 0 days.

(21) Appl. No.: 12/636,143

(22) Filed: Dec. 11, 2009

(65) Prior Publication Data

US 2011/0064765 A1 Mar. 17, 2011

Related U.S. Application Data

(62) Division of application No. 12/066,090, filed as application No. PCT/EP2006/066161 on Sep. 8, 2006, now abandoned.

(30) Foreign Application Priority Data

Sep. 9, 2005 (EP) .................................... 05108299

(51) Int. Cl.
*C12Q 1/68* (2006.01)
(52) U.S. Cl. .......................................... 435/5; 435/345
(58) Field of Classification Search .................. None
See application file for complete search history.

(56) References Cited

U.S. PATENT DOCUMENTS

| 5,925,359 A * | 7/1999 | Van Woensel et al. .... 424/204.1 |
| 6,703,023 B1 * | 3/2004 | Jestin et al. ................. 424/204.1 |
| 7,223,407 B2 * | 5/2007 | Jestin et al. ................. 424/199.1 |

FOREIGN PATENT DOCUMENTS

WO 03049703 6/2003

OTHER PUBLICATIONS

Opriessnig et al, Clinical and Vaccine Immunology, Mar. 2008 [Available online on Dec. 19, 2007]; vol. 15, No. 3, pp. 397-401.*
Tischer et al, Archives of Virology, 1995, vol. 140; pp. 737-743.*
Blanchard, P. et al., Vaccine, 21:4565-4575 (2003).
Kamstrup, S. et al., Vaccine, 22:1358-1361 (2004).
Siegrist, C-A., Vaccine, 21:3406-3412 (2003).
Chae, C., The Veterinary Journal, 169:326-336 (2005).

* cited by examiner

*Primary Examiner* — Ali R. Salimi
(74) *Attorney, Agent, or Firm* — William M. Blackstone

(57) ABSTRACT

The present invention relates to a vaccine and a method for protecting piglets against PCV-2 infection by administering a vaccine comprising at least 20 micrograms/dose of ORF-2 protein of porcine circovirus type 2, even when they have a relatively high titer of maternally derived antibodies against PCV-2. A vaccine according to the invention may contain a recombinant ORF-2 protein, wherein said recombinant protein is preferably produced by way of expression from a baculovirus expression vector in insect cells, said baculovirus expression vector containing the PCV-2 ORF-2 gene sequence under control of a suitable promoter.

8 Claims, No Drawings

PCV-2 VACCINE

This application is a Divisional application of U.S. Ser. No. 12/066,090 filed Mar. 7, 2008, now abandoned, which is the U.S. National Phase Application of PCT/EP2006/066161 filed Sep. 8, 2006, which is the International Application based on European Application EPO 05108299.8 filed Sep. 9, 2005, all of which are relied on for priority and are incorporated herein by reference in their entirety.

PCV-2 is thought to be linked to the post-weaning multisystemic wasting syndrome (PMWS) observed in young pigs.

This disease was encountered for the first time in Canada in 1991.

The clinical signs and pathology were published in 1997 (Clark et al. Proc. Am. Assoc. Swine. Pract, 1997: 499-501, Harding et al., Proc. Am. Assoc. Swine. Pract, 1997:503.), and include progressive wasting, dyspnea, tachypnea, and occasionally icterus and jaundice.

Nayar et al., Can. Vet. J. Volume 38, June 1997 detected Porcine Circovirus in pigs with clinical symptoms of PMWS and concluded that a PCV, other then the known PCV recognized as a natural inhabitant of PK-15 cells, could be linked to PMWS. Later publications (Hamel et al., J. Virol., 72(6), 5262-5267, 1998; Meehan et al., J. gen. Virol., 79, 2171-2179, 1998) confirmed these findings, and it was proposed (Meehan et al., supra) to refer to the new pathogenic PCV as PCV-2, whereas the original PK-15 cell culture isolate (Tischer et al., Nature 295, 64-66, 1982), should be referred to as PCV-1.

PCV1 and PCV-2 are small (17 nm) icosahedral non-enveloped viruses containing a circular single stranded DNA genome. The length of the PCV-2 genome is about 1768 bp. PCV-2 isolates originating from different regions in the world seem to be closely related to each other and display 95 to 99% nucleotide sequence identities (Fenaux et al., J. Clin. Micorbiol., 38(7), 2494-2503, 2000). ORF-2 of PCV encodes the putative capsid protein of the virus. The ORF 2 of PCV 2 encodes a protein of 233 amino acids. The ORF 2 of all PCV-2 isolates share 91-100% nucleotide sequence identity and 90-100% deduced amino acid sequence identity. Between the ORF 2 genes of PCV 1 and PCV-2 there exists only 65 to 67% nucleotide identity and 63 to 68% amino acid sequence identity (Fenaux et al., supra).

PDNS (porcine dermatitis and nephropathy syndrome) is another major problem for pig farmers which appeared around the same time as PMWS. Characteristic of PDNS are red/brown circular skin lesions with haemorrhages, usually on the ears, flanks, legs and hams. A review of PCV-2 related syndromes and diseases is given in Chae. C (2005) Vet. J. 169 326-336.

There is a need for a vaccine that protects piglets against PCV-2 related diseases such as PMWS and PDNS. However, as of yet there is no commercially available vaccine against PCV-2 related diseases.

Traditionally one would think of a conventional vaccine for pigs based on inactivated whole PCV-2 virus. However, in the case of PCV-2 matters are complicated by the fact that PCV-2 does not replicate to high titers in cell culture.

As an alternative a vaccine could be based on recombinant antigens derived from PCV-2. PCV-2 proteins have already been expressed in various expression systems. For example, Liu et al. (Protein Expression and Purification, 21, 115-120 (2001) expressed a fusion protein of the entire protein encoded by ORF-2 of PCV-2 linked to a MBP His tag, in *E. coli*. Kim et al. (J. Vet. Sci, 3(1), 19-23, 2002) expressed ORF 1 and 2 of PCV 2 in a baculovirus expression system. Blanchard et al. (Vaccine, 21, 4565-4575, 2003) expressed ORF 1 and ORF 2 in baculovirus based system in insect cells as well. The insect cells which had produced the PCV-2 proteins were lysed and formulated into a vaccine which was used to vaccinate specific pathogen free (SPF) piglets. The piglets received either one of the proteins in a prime boost regimen where the subunit vaccine followed a DNA vaccination or, in another group of piglets, the piglets received the ORF 1 and ORF 2 protein in two injections. However, all experiments were carried out with SPF pigs which are pathogen free and thus do not have any maternally derived antibodies against PCV-2.

PMWS and PDNS caused by PCV-2 can be observed from 4 weeks of age until about 15 weeks of age. It seems that until weaning the piglets are quite safe from PCV-2 related diseases, only after weaning do piglets have a chance of getting clinical symptoms.

As a consequence, to protect piglets with vaccination, the piglets will ideally have to be protected from weaning onwards since it is unpredictable when PCV-2 related diseases will manifest.

To achieve this with a two shot vaccination regime, the piglets need to obtain their priming vaccination already in the first week(s) of age so they can receive the booster vaccination round the time of weaning and have obtained full protection against PCV-2 infection just after weaning.

Piglets are likely to have maternally derived antibodies (MDA) against PCV-2. (A distribution of MDA titers in piglets used in experiments with a vaccine according to the invention is given in the Examples). It is however, well known that the presence of maternally derived antibodies will interfere with vaccination.

Piglets may have different titers of MDA. Very high passive MDA titers may protect the piglets against PCV-2 infection (Merial: "PCV-2 Diseases: From research back to the field strain", 18$^{th}$ IPVS, Hamburg Germany, June 2004, page 99-101).

However piglets with lower MDA titers will not be protected against PCV-2 infection when they have reached the relevant age (i.e. post weaning).

For those piglets, which seems to be the majority encountered in the field, the MDA titer may be too low to provide protection against PCV-2 infection, while still high enough to interfere with vaccination with, for example, a conventional inactivated PCV-2 vaccine. Especially since an inactivated vaccine may contain less antigen due to the fact that the virus can not be propagated to high titers in cell culture (or complicated and time consuming concentration procedures should be introduced in vaccine production). Especially for this group of piglets a vaccine according to the invention has been found to provide adequate protection against PCV-2 infection.

With the present invention, a vaccine has been provided that can be used in a method to protect piglets, even piglets which are MDA positive against PCV-2, against infection with PCV-2, and thus against PCV-2 related diseases, most notably PMWS and PDNS.

The present invention provides a vaccine against PCV-2 comprising at least 20 microgram/dose of ORF-2 protein of porcine circovirus type 2 (PCV-2).

It has been found that a vaccine containing at least 20 microgram (ug) of ORF-2 protein of PCV-2 per dose is capable of eliciting a protective immune response against PCV-2 infection (and thus against PCV-2 related diseases like PMWS and PDNS) even in the face of MDA. Preferably the vaccine contains at least 50 ug per dose, and most preferably 80 ug per dose. Vaccines according to the present invention with an antigenic mass up to 275 ug per dose could even be prepared, and such vaccines still did not elicit local reactions at the injection site. Of course even more micrograms of antigen can be put in a vaccine dose of a vaccine according to the invention, but if the protection obtained with the vaccine is not improved with a higher dose the increase in antigenic load only results in the vaccine being more expensive than necessary. In addition an increasing dose of antigen may eventually lead to unacceptable local reactions at the injection site, which should be avoided. A method to measure the antigenic mass is given in the experimental part of this application.

A vaccine according to the invention may contain a recombinant ORF-2 protein, wherein said recombinant protein is preferably produced by way of expression from a baculovirus expression vector in insect cells, said baculovirus expression vector containing the PCV-2 ORF-2 gene sequence under control of a suitable promoter.

Although other suitable expression systems known in the art may be used as well in a method to prepare a vaccine according to the invention, it has been found that the use of the baculo expression system results in the production of high yields of viral antigen, which moreover show a good antigenicity. The use of the baculo expression system thus eliminates the need for complicated and time consuming procedures to concentrate the antigen to a suitable level when it cannot be produced at a high concentration, for example in a virus infected cell culture.

The most commonly used baculo expression vector is *Autographa californica* often used with an insect cell culture of SF-9, SF-21 or High five insect cells. SF-9 and SF-21 are ovarian cell lines from *Spodoptera frugiperda*, High five cells are derived from egg cells from *Trichoplusia ni*. The PCV-ORF-2 gene should be placed under the control of a suitable promoter. Most commonly used promoters in the baculovirus expression system are the promoters for the polyhedrin gene and the promoter for the p10 gene, meaning that the ORF-2 PCV-2 gene sequence is inserted in an insertion site in either the polyhedron locus or the p10 locus in the baculovirus genome. Other suitable promoters, either homologous or heterologous, known in the art may be used as well. A detailed description of all aspects of the baculovirus expression system is given in "Baculovirus Expression vectors" by D. R. O'Reilly, L. K. Miller, and V. A. Luckow (1992, W.H. Freeman & Co, New York). Furthermore baculovirus derived expression vectors and complete expression systems are commercially available from many different companies.

A vaccine according to the invention may further comprise a suitable adjuvant. Many adjuvant systems are known in the art, for example commonly used oil in water adjuvant systems. Any suitable oil may be used, for example a mineral oil known in the art for use in adjuvantia. The oil phase may also contain a suitable mixture of different oils, either mineral or non-mineral. Suitable adjuvantia may also comprise vitamin E, optionally mixed with one or more oils. The water phase of an oil in water adjuvanted vaccine will contain the antigenic material. Suitable formulations will usually comprise from about 25-60% oil phase (40-75% water phase). Examples of suitable formulations may comprise 30% water phase and 70% oil phase or 50% of each.

A vaccine according to the invention may be administered via any suitable route known in the art such as intramuscularly, intradermally or subcutaneously, whereby intramuscular administration is preferred.

The present invention further provides a method for the manufacture of a vaccine intended for the protection of young piglets, which are PCV-2 MDA positive, against PCV-2 infection, wherein said vaccine is provided with at least 20 ug/dose of ORF-2 protein of porcine circovirus type 2 (PCV-2).

A vaccine (prepared by a method) according to the invention can be used in a method to protect young piglets against PCV-2 infection.

A vaccine according to the invention can even be used in a method for the protection of young piglets, which are positive for maternally derived antibodies (MDA) against PCV-2, against infection with PCV-2.

It has been found that a vaccine according to the invention can protect piglets, even when they have a relatively high titer of MDA against PCV-2. A distribution of MDA titers in young piglets encountered in the field at various farms across Europe are reflected in table 1, and the protection provided by a vaccine according to the invention is reflected in table 2.

It has been shown that a vaccine according to the invention can even provide adequate protection against PCV-2 infection to piglets that have MDA titers falling in "cluster 2" as defined in the Examples (Table 2). Piglets falling in this cluster have MDA titers between 8 and 12 log 2 which is a high MDA titer.

A vaccine according to the invention can therefore even be used in a method for the protection of young piglets, which have an MDA titer against PCV-2 up to 10 log 2, or even 12 log 2 (as measured with a method as indicated in the Examples).

From Table 1 it can be seen that about 55% of the piglets collected at various farms over Europe fall within this cluster 2 (while of course piglets falling within cluster 1, which have a lower MDA titer and which comprise 32% of the population, are also protected by a vaccine according to the invention). Thus it can be concluded that a vaccine according to the invention provides protection to the vast majority of piglets encountered in the field, including those with high MDA titers.

To provide adequate protection the vaccine is preferably administered in a 2 shot vaccination regimen, whereby the first shot (priming vaccination) is given to the piglets in the first to fourth week of age, preferably prior to weaning, for example in the first week of age. The second shot (boosting vaccination) can be given about 3 weeks later. In this way the piglets will have obtained full protection against PCV-2 infection just after weaning which is when the piglets are most susceptible to PCV-2 infection and thus become susceptible to PMWS and PDNS.

EXAMPLES

Example 1

(Determination of Maternally Derived) PCV-2 Specific Antibody Titers

Antibody titers against PCV-2 can be determined in the following manner:

A monolayer of PK15 cells was formed in 96-well tissue culture plate. At 80% confluency the cells were infected with a field isolate of PCV-2 and further incubated for 2 days at 37° C. in a $CO_2$ incubator. After this period the cells were fixed in Ethanol and stored at 2-8° C. until use. Plates are used for tests when approximately 20% of the cells were infected.

To determine the PCV-2 specific antibody titre of a given serum, serial dilutions are made and incubated on the ethanol fixated cells. After 1 hour of incubation at 37° C. the plates are washed with tap water and the bound antibodies detected by incubation with FITC-labeled Rabbit anti-Swine IgG. The titre of a given serum is expressed as the reciprocal of the highest dilution where a PCV-2 specific antibody response can still be observed.

A typical distribution of the maternally derived antibody titers against PCV-2 in pre-weaning piglets is given in table 1.

Sera were collected from 232 piglets from various countries across Europe.

TABLE 1

The distribution of maternally derived antibody titres in a group of 232 young piglets

| Categories of piglets with PCV-2 specific maternally derived antibody titres (log2) in a population | Percentage of piglets per category | Percentage of piglets per cluster |
|---|---|---|
| ≤4 | 1.3 | 32 |
| 5 | 9.9 | |
| 6 | 9.1 | |
| 7 | 12.1 | |
| 8 | 9.5 | 55 |
| 9 | 19.4 | |
| 10 | 11.2 | |
| 11 | 9.9 | |
| 12 | 4.7 | |
| 13 | 5.2 | 13 |
| 14 | 3.0 | |
| 15 | 2.6 | |
| 16 | 1.3 | |
| ≥17 | 0.8 | |

In table 1 three clusters can be distinguished: Cluster 1; piglets with titres smaller than 8, cluster 2; piglets with titres from 8 to 12 and cluster 3; piglets with titres of 13 and higher. In cluster 3 the maternally derived antibody titres are that high that it is expected that the piglets will be protected during the critical period of age (Merial: "PCV-2 Diseases: From research back to the field strain", $18^{th}$ IPVS, Hamburg Germany, June 2004, page 99-101). In cluster 1 however, the maternally derived antibody titres are that low that most of these piglets can be easily vaccinated. However, in cluster 2 the antibody titres are of such a magnitude that a conventional vaccination approach will probably fail to immunize the majority of this group. Since more than halve of the piglets seem to fall into this cluster it will be of the uttermost importance to be able to protect the piglets in this cluster if one wants to eliminate PMWS from a farm.

It is well known in the art that vaccination in the face of maternally derived antibody titres can be helped by an adjuvant and or a high antigen content. It is not known which adjuvant or which antigen content will be able to break through the maternally derived antibody titres directed against a given pathogen. Therefore, in the experiments described we sought to define the minimal amount of antigen that would be needed to protect the piglets in cluster 2 against a PCV-2 infection Example 2

Construction of a Recombinant Baculovirus Expressing PCV-2 ORF-2

PCV-2 virus was isolated from lung tissue of a feeder pig showing clinical and histopathological signs of PMWS using PCV-free Swine Testis (ST) cells. The virus was propagated through five passages on PCV-free PK15 cells.

DNA was isolated from a preparation of PCV-2 virus purified from infected PK15 cell supernatant. PCR was done to amplify the ORF-2 gene based on published sequences, using primers containing BamH1 restriction sites (forward primer: CGG GAT CCG TTT TCA GCT ATG ACG TAT [SEQ ID NO.:1], reverse primer: CGG GAT CCT TTA TCA CTT CGT AAT GGT T [SEQ ID NO.: 2]). The resulting amplicon encompasses the complete ORF-2 gene plus flanking BamH1 restriction sites.

Following gel electrophoresis, the amplicon was excised and purified. The purified PCV-2 ORF-2 fragment was then digested with BamH1, and ligated into BamH1-digested pAcAS3 (Vlak et al. (1990) *Virology* 179 312-320). This plasmid contains the p10 promotor upstream of the insertion site, allowing for expression of foreign genes under control of the p10 promotor.

TOP 10F' bacteria (Invitrogen, Carlsbad, USA) were transformed with the ligation mixture, and clones which contained the correct construct were selected based on their sequence. A positive clone was expanded and the transfer plasmid DNA was again retested using sequencing.

Before transfection, *Autographa californica* nuclear polyhedrosis virus (AcNPV, described in Martens et al. (1995) *J. Virol. Methods* 52 15-19) was digested with Bsu36I. The Bsu36I site in this virus is a unique restriction site in the p10 locus.

*Spodoptera frugiperda* (Sf9) cells were then transfected with transfer plasmid and Bsu36I-digested AcNPV baculovirus DNA using CellFectine (Life Technologies, Gaithersburg, USA). The supernatant of the transfection was harvested at 3 days post transfection and plaque purifications were performed on Sf9 cells.

Plaques were expanded and the resulting virus was screened for PCV-2 ORF-2 gene insertion by sequencing of isolated viral DNA, and immunofluorescence on Sf9 cells using anti-PCV-2 rabbit and pig sera.

A seed of recombinant baculovirus BacPCV-2-ORF-2 was prepared called "Masterseed". The Masterseed and the $5^{th}$ passage of the Masterseed on Sf9 cells were tested for stable insertion of the PCV-2 ORF-2 gene by sequencing of isolated DNA and immunofluorescence on Sf9 cells.

Titrations were done to measure the amount of infectious virus in the virus preparations. Titrations were done on Sf9 cells, and were read by observing baculovirus specific CPE and/or PCV-2 ORF-2 specific immunofluorescence using polyclonal rabbit anti-PCV-2 immune serum.

It was demonstrated that a plaque-purified Masterseed of recombinant AcNPV baculovirus BacPCV-2-ORF-2 was produced. This construct stably expressed the PCV-ORF-2 protein under control of the p10 promotor on Sf9 cells as judged by sequencing and immunofluorescence of the Masterseed and the $5^{th}$ passage from the Masterseed on Sf9 cells.

Example 3

Production of PCV-2 Antigen

In order to obtain maximum amounts of expression product, pilot experiments were carried out to optimize the conditions for obtaining recombinant PCV-2 ORF-2 protein. All experiments were carried out using *Spodoptera frugiperda* 21 (Sf21) cells in suspension culture at 28° C. BacPCV-2-ORF-2 virus at the $4^{th}$ passage level from the Masterseed was used for infection. For optimized production, cell density at the time of infection was $1.4 \times 10^6$ cells/ml, the multiplicity of infection (MOI) was 0.01 and culture was continued for 6 days following infection. The resulting mixture was named expression product harvest. Expression under optimized conditions was carried out 5 times in separate experiments during the course of one year.

Since the antigen was located in the cells the total harvest containing both cells and supernatant was subjected to sonication to the extent that at least 90% of the cells were disrupted. Thereafter the live recombinant virus in batches of sonicated harvest was inactivated with 33 mM Binary Ethylenimine (BEI) at 37° C. for 72 hours under continuous stirring, at a pH of 7.5. After inactivation, the BEI was neutralized by the addition of a 1.6 fold molar excess of Sodium Thiosulphate.

After neutralization, cell debris and polyhedra were removed by low-speed centrifugation at 600 g for 10 min. The resulting supernatant was named inactivated virus suspension. Harvests were checked for sterility and for completeness of inactivation. Completeness of inactivation was tested by passaging inactivated virus suspension on Sf9 cells for 2 weeks and visual inspection for the absence of baculovirus specific CPE.

It was demonstrated that Baculovirus titres of was 8.5 $\log_{10}$ $TCID_{50}$/ml were obtained which were completely inactivated after treatment with BEI.

Example 4

Determination of the Amount of PCV-2 Antigen

Samples of inactivated suspension before and after low-speed centrifugation, and a cell culture supernatant sample of parent transfer virus were subjected to denaturing SDS-polyacrylamide gel-electrophoresis according to the method of Laemmli (Laemmli, U. K. (1970). *Nature* 227, 680-685). A 4-12% gradient gel was used, which was stained with Coomassie Brilliant Blue.

When Western Blotting was done, the proteins from the gel were electrophoretically transferred onto Nylon membranes, blocked with skimmed milk in PBS, and reacted with diluted polyclonal Swine serum raised against a field isolate of PCV-2.

As a measure of the antigen content of the resulting inactivated virus suspension, 1 microliter (ul) of this suspension was run on a gel in a similar manner, while serial dilutions of Bovine Serum Albumin (Sigma, St. Louis, USA. cat. no. A-2153) were run in parallel on the same gel as a reference. Quantification of the ORF-2 gene product in the inactivated virus suspension was done by comparing the densities of the BSA reference with that of the PCV-2 containing sample by using camera capture imaging and computerised analysis using GeneTools (SynGene, Cambridge, UK. v. 3.06.02).

When inactivated harvests before and after low-speed centrifugation were compared by electrophoretic separation on SDS-PAGE gels against Precision Plus markers (Bio-Rad, Hercules, USA), the material before centrifugation gave 2 major bands of approximately equal density of apparent Molecular Weights (MW) of 30 and 26.8 kDa, while the material after centrifugation only contained the lower band. When parent transfer virus was run alongside the recombinant virus, the parent transfer virus only contained the higher of the two bands, demonstrating that the lower band was the ORF-2 of PCV and the higher band the polyhedrin that was removed after centrifugation.

The identity of the lower 26.8 kDa band was further confirmed by Western Blotting, where it was shown that this band, but not the 30 kDa band, reacted with polyclonal Swine serum raised against PCV-2 field virus.

Expression levels of the PCV-2 ORF-2 were determined in 5 separate experiments, and in each instance, the amount was well above the detection limit of the test, specifically ranging from 40 to 550 microgram/milliliter (ug/ml) of inactivated virus suspension.

Example 5

Influence of the Amount of PCV-2 ORF-2 on Vaccine Take in MDA Positive Young Piglets Vaccines of different PCV-2 ORF-2 antigen content were formulated and used to vaccinate young piglets with varying levels of maternally derived antibodies (MDA) against PCV-2. Two vaccinations were given, 3 weeks apart. The seroresponse against the antigen was measured at 5-6 weeks after the first vaccination. From these data, the influence of the antigen content on the take of the vaccine in the face of MDA was calculated.

Various antigen dilutions were made and mixed 1:1 (v/v) with an oil-in-water adjuvant, such as are common in the art.

Then, at between 1 and 4 weeks of age, litters were divided into groups and treated intramuscularly with vaccines containing varying amounts of PCV-2-ORF-2 protein, or were not vaccinated. Vaccinations were repeated after 3 weeks. The following groups were made:

114 piglets vaccinated with 1-14 ug of PCV-2 ORF-2 protein/dose (group 1), 85 piglets vaccinated with 20 and 80 ug/dose (group 2)

Blood was taken at the time of first vaccination, and at 5-6 weeks thereafter. Sera were prepared and examined for PCV-2 antibodies by immunofluorescence. For this a monolayer of PK15 cells in a 96-well tissue culture plate was infected with a field isolate of PCV-2. After 2 days of culture, when approximately 20-30% of the cells were infected, the monolayers were fixed in Ethanol and stored at 2-8° C. until use. To determine the titre, serial dilutions of test sera were incubated on the cells for 1 hour at 37° C., and after washing of the plates, bound antibodies were detected by incubation for 1 hour at 37° C. with FITC-labeled Rabbit anti-Swine IgG (Nordic, Tilburg, The Netherlands). Titres were determined as the reciprocal of the highest dilution where a PCV-2 specific fluorescence could still be observed.

For all animals, the decline of the antibody titer between the first and second bleeding was determined. If in this period the antibody titre had not declined or was increased it was regarded that in the animal concerned the vaccine had taken. However when the PCV-2 specific antibody titre was decreased it was regarded that vaccination had not succeeded and the vaccine didn't take.

By relating the take of various vaccine doses to the maternally derived antibody titre at time of vaccination the minimal antigenic mass needed to vaccinate a sufficient amount of piglets could be determined. The results of this analysis are given in Table 2.

TABLE 2

Percentage of vaccine take at various MDA titres and antigen concentrations.

| Categories of piglets with PCV-2 specific maternally derived antibody titres (log2) at vaccination | Group 1; 1-14 ug/dose | | Group 2; 20-80 ug/dose | |
|---|---|---|---|---|
| | Number of piglets per category/number of piglets were the vaccine took | Percentage vaccine take per cluster | Number of piglets per category/number of piglets were the vaccine took | Percentage of vaccine take per cluster |
| ≦4 | 3/3 | 90% | 1/1 | 100% |
| 5 | 0/0 | | 3/3 | |
| 6 | 15/13 | | 5/5 | |
| 7 | 2/2 | | 3/3 | |
| 8 | 12/8 | 17% | 4/4 | 76% |
| 9 | 12/5 | | 11/10 | |
| 10 | 6/0 | | 13/10 | |
| 11 | 21/0 | | 15/10 | |
| 12 | 26/0 | | 7/4 | |
| 13 | 15/0 | 0% | 6/1 | 4% |
| 14 | 2/0 | | 11/0 | |
| 15 | 0/0 | | 4/0 | |
| 16 | 0/0 | | 1/0 | |
| ≧17 | 0/0 | | 1/0 | |
| Total | 114/31 | 27% | 85/51 | 60% |
| Total protected* | 114/48 | 42% | 85/73 | 86% |

*the total number of piglets protected is given by the number of piglets where the vaccine has taken in piglets with a titre smaller than 13 plus the piglets that already have a titre of 13 or higher.

In this table, "vaccine take" means that the vaccination of a piglet resulted in a PCV-2 specific antibody titre at 1 week post booster vaccination that is equal or higher than the PCV-2 specific titre at primary vaccination. In all such cases it is demonstrated that the vaccine mounted an active serum response against PCV-2 and in which case piglets can be regarded as being protected against a PCV-2 infection. However, in piglets where the titre at 1 week post booster was smaller than at primary vaccination the vaccine was unable to induce an immune response and the natural decline of maternally derived antibodies was observed which, in time, will render these animals susceptible for a PCV-2 infection.

From the table it is demonstrated that when using vaccine doses equal or smaller than 14 microgram, in cluster 1 (MDA tritres ≦7) 90% of the animals will seroconvert due to vaccination and can therefore be regarded as being protected. However, in cluster 2 (MDA titres >7 and <13), only 17% of the animals vaccinated with a dose smaller or equal to 14 microgram seroconverted and were protected. In this group 17 animals had titres of 13 or larger and where therefore, already protected by their naturally acquired PCV-2 specific maternally derived antibodies. Therefore, one can conclude that in this group of a total of 114 piglets only 48 (42%) were protected; 17 piglets with already high maternally derived antibody titres plus 31 seroconverted piglets in clusters 1 and 2.

In the group vaccinated with 20 micrograms per dose or more, significantly more animals were protected; all the animals in cluster 1 and 76% of the animals in cluster 2 seroconverted for PCV-2 and were hence protected adding to this the piglets with MDA titres of 13 or more it was found that 88% of the piglets in this group were protected.

Since herd protection is obtained when about 80% or more of the animals are protected it can be concluded that the antigenic mass of a vaccine directed against PCV-2 must at least contain 20 ug of antigen or more to be able to efficiently protect a herd against the consequences of a PCV-2 infection.

The invention claimed is:

1. A method for the protection of piglets that are Porcine circovirus type 2 (PCV-2) maternally derived antibody (MDA) positive against PCV-2 infection, comprising administering a vaccine comprising at least 20 micrograms/dose of ORF-2 protein of PCV-2.

2. The method according to claim 1, comprising at least 50 micrograms/dose of ORF-2 protein of porcine circovirus type 2(PCV-2).

3. The method according to claim 1, wherein the ORF-2 protein is a recombinant protein.

4. The method according to claim 1, wherein the ORF-2 protein is produced by way of expression from a baculovirus expression vector in insect cells, said baculovirus expression vector containing the PCV-2 ORF-2 gene sequence under control of a suitable promoter.

5. The method according to claim 4, wherein the promoter is the p10 promoter.

6. The method according to claim 1, wherein the vaccine further comprises a suitable adjuvant.

7. The method according to claim 6, wherein the adjuvant is an oil in water emulsion.

8. The method according to claim 6, wherein the adjuvant contains vitamin E.

* * * * *

SEQUENCE LISTING

<160> NUMBER OF SEQ ID NOS: 2

<210> SEQ ID NO 1
<211> LENGTH: 27
<212> TYPE: DNA
<213> ORGANISM: Porcine circovirus

<400> SEQUENCE: 1
cgggatccgt tttcagctat gacgtat                27

<210> SEQ ID NO 2
<211> LENGTH: 28
<212> TYPE: DNA
<213> ORGANISM: Porcine circovirus

<400> SEQUENCE: 2
cgggatcctt tatcacttcg taatggtt               28